United States Patent [19]

Koulbanis et al.

[11] Patent Number: 5,560,916
[45] Date of Patent: Oct. 1, 1996

[54] COSMETIC COMPOSITION CONTAINING VINEGAR AS ACTIVE ANTI-AGEING AGENT, AND ITS USE IN THE TREATMENT OF DERMATOLOGICAL AGEING

[75] Inventors: Constantin Koulbanis, Le Kremlin-Bicetre; Myriam Mellul, L'Hay-les-Roses; Didier Candau, Bievres, all of France

[73] Assignee: L'Oreal, Paris, France

[21] Appl. No.: 383,429

[22] Filed: Feb. 3, 1995

[30] Foreign Application Priority Data

Feb. 4, 1994 [FR] France .................. 94 01281

[51] Int. Cl.⁶ .................. A61K 7/48; A61K 31/74; A23L 1/221
[52] U.S. Cl. .................. 424/401; 424/78.03; 424/195.1; 426/650; 514/844; 514/936; 514/944
[58] Field of Search .................. 424/78.03, 401, 424/195.1; 514/844, 936, 944; 426/650

[56] References Cited

U.S. PATENT DOCUMENTS

| | | |
|---|---|---|
| 4,255,418 | 3/1981 | Bailey . |
| 4,595,591 | 6/1986 | Mordi et al. .................. 514/844 |
| 5,006,557 | 4/1991 | Siu-Ming . |

FOREIGN PATENT DOCUMENTS

| | | |
|---|---|---|
| 0177985 | 4/1986 | European Pat. Off. . |
| 2229105 | 11/1990 | European Pat. Off. . |
| 52-105224 | 9/1977 | Japan . |
| 02229105 | 9/1990 | Japan . |
| WO88/08701 | 11/1988 | WIPO . |
| WO89/02223 | 2/1989 | WIPO . |
| WO92/18595 | 10/1992 | WIPO . |

OTHER PUBLICATIONS

French Search Report No. FA 495286, dated Nov. 11, 1994.

*Primary Examiner*—Carlos Azpuru
*Attorney, Agent, or Firm*—Oblon, Spivak, McClelland, Maier & Neustadt, P.C.

[57] ABSTRACT

A cosmetic or dermatological composition for use in the treatment of ageing of the skin is provided which contains vinegar as the active anti-ageing agent in a cosmetically or dermatologically acceptable carrier, along with a method for the treatment of ageing, exemplified by wrinkles and/or lines and/or blemishes, using the composition.

11 Claims, No Drawings

COSMETIC COMPOSITION CONTAINING VINEGAR AS ACTIVE ANTI-AGEING AGENT, AND ITS USE IN THE TREATMENT OF DERMATOLOGICAL AGEING

BACKGROUND OF THE INVENTION

1. Field of the Invention

The present invention relates to the use of vinegar in a cosmetic or dermatological composition for combating ageing, and a method for treatment of ageing using the composition.

2. Discussion of the Background

For a number of years now, cosmetic compositions have appeared on the market which contain α-hydroxy acids such as glycolic, malic and lactic acids, for combating the visible signs of ageing, especially wrinkles, linear dull complexion and blemishes, and for eliminating blackheads caused by acne. These compositions are generally presented in the form of creams or lotions.

In order to be active, such compositions must contain the α-hydroxy acid in its acid form (cf. in particular the article by W. P. Smith, Soap Cosmetic Chemical specialties, September 1993, pp. 54–58 and 76: "Hydroxy acids and skin aging"). This gives the composition a low pH, causing problems of skin tolerance which manifest themselves to the user as instances of stinging, reddening and pulling, which may lead to considerable discomfort.

Accordingly, it is desired to find active agents which have the same effect as α-hydroxy acids without the above noted negative side effects.

It in known to use vinegar, in particular in the form of a rinsing solution, as a skin-cleansing agent, as an antiseptic and as an astringent tonic (cf. "Les vinaigres"0 [Vinegars], Centre intercontinental d'études de techniques biologiques, 1964, pp. 13–15).

Moreover, EP-A-177 985 describes an antiseptic product based on vinegar and honey. The incorporation of vinegar into shampoos and soaps for the treatment of herpes and eczema is also known (JP-A-62-135 597), as is its incorporation into compositions which are intended to stimulate the regrowth of hair (FR-A-2 636 528, GB-A-2 159 053, DE-A-35 33 121). In addition, EP-A-297 640 describes a composition based on herbs, as an infusion in vinegar, for the treatment of psoriasis and hair loss, and JP-A-02-229 105 relates to a whitening composition which contains an extract of egg yolk which has macerated in vinegar and which has then been extracted in an organic solvent before being used in the form of a yellow powder.

However, there is no mention in any of these documents of the use of vinegar as an active agent to reduce or even eliminate, the signs of skin ageing.

SUMMARY OF THE INVENTION

Accordingly, one object of the present invention is to provide a cosmetic or dermatological composition for use in treatment of the aging of skin which contains vinegar as the active anti-ageing agent.

Another object of the present invention is the use of a cosmetic composition containing vinegar for combating wrinkles and/or lines and/or dull complexion and/or blemishes.

Another object of the present invention is the use of vinegar for the preparation of a dermatological composition for treating blemishes which are morbid in origin.

Another object of the present invention is to provide a method for the cosmetic treatment of ageing, using the vinegar containing composition of the present invention.

These and other objects of the present invention have been satisfied by the discovery that vinegar, and more particularly wine vinegar, can be incorporated in a cosmetic or dermatological composition to be used in the treatment of aging, as characterized by wrinkles, lines, dull complexion and blemishes.

DETAILED DESCRIPTION OF THE PREFERRED EMBODIMENTS

The present invention relates to a cosmetic or dermatological composition for use in the treatment of ageing, comprising an effective amount of vinegar as an active anti-ageing agent in a cosmetically acceptable carrier. Within the context of the present invention, ageing includes the ageing of the skin, whether cosmetic or dermatological in origin.

The present invention further relates to a method for the cosmetic treatment of ageing, comprising applying, to the skin of a subject in need thereof, an effective anti-ageing amount of a cosmetically acceptable composition comprising vinegar as the active anti-ageing agent in a cosmetically acceptable carrier.

Vinegar is the fermentation product of alcohol, containing, inter alia, acetic acid, and wine vinegar is the product obtained by the fermentation of wine. It is therefore a natural biological product. In the present composition, it is also possible to use, for example, cider vinegar, lemon vinegar, blackberry vinegar and raspberry vinegar.

Regardless of its origin, vinegar has a natural acidity which is due principally to acetic acid, which makes up from 4 to 18% of its composition. Vinegar additionally comprises 10 inorganic salts, in particular those of zinc, potassium, lithium and sodium; sugars, in particular glucose, fructose and xylitol; ethanol, and vitamins (vitamins B and D in particular). It is in the form of a clear solution whose color varies from orange-yellow to red.

In the composition of the present invention, the preferred vinegar is wine vinegar.

Vinegar has the advantage of being active for treating ageing while being tolerated better than the α-hydroxy acids which are traditionally used. In fact, vinegar has a pH which is higher than the α-hydroxyacids: the pH of wine vinegar, which contains 6% acetic acid, is 2.7, as compared to 1.74 for a 6% solution of lactic acid. Moreover, vinegar has a certain buffering power, as in the pH of wine vinegar ranges from 2.7 for pure vinegar to 3.0 for a 10% vinegar solution.

The composition according to the present invention contains an effective anti ageing amount of vinegar, preferably from 0.5% to 50% by weight of vinegar, relative to the total weight of the composition, and most preferably from 3% to 10% by weight.

The compositions according to the invention may be in any of the conventional pharmaceutical forms which are normally employed for topical application, such as aqueous gels, oil-in-water (O/W) or water-in-oil (W/O) emulsions, lotions, ointments, solutions, or dispersions of spherules, especially those which are lipid in nature.

In particular, the emulsions may be present in the form of creams, milks, foundations and tinted creams. In these latter cases the composition also may contain cosmetically acceptable pigments and/or dyes.

The emulsions may additionally contain lipid vesicles.

In addition to vinegar, the cosmetic or dermatological compositions of the present invention may contain, if desired, water, emulsifiers, oils and adjuvants which are customary in the cosmetics field. These customary adjuvants include, but are not limited to, hydrophilic or lipophilic gelling agents, hydrophilic or lipophilic active agents, preservatives, antioxidants, fragrances, fillers, screening agents and colorants. The quantities of these various adjuvants are those which are conventionally employed in the cosmetics and/or dermatological field, and preferably range from 0.01% to 10% of the total weight of the composition. Depending on their nature, these adjuvants may be introduced into the fatty phase, into the aqueous phase and/or into the lipid vesicles.

The names of the compounds which follow are given in the CTFA nomenclature (International Cosmetic Ingredient Dictionary).

Emulsifiers which can be used are water-in-oil (W/O) or oil-in-water (O/W) emulsifiers, depending on the final emulsion desired. A preferred W/O emulsifier is the 4-polyglyceryl isostearate/cetyldimethicone copolyol/hexyl laurate mixture sold under the name Abil WE 09 by the company Goldschmidt.

Preferred O/W emulsifiers include the PEG-40 stearate sold under the name Myrj 52 by the company ICI, the sorbitan tristearate sold under the name Span 65 by the company ICI, or the sorbitan stearate sold under the name Span 60 by the company ICI.

The proportion of emulsifier may range from 0.1% to 10% by weight, and preferably from 0.5% to 5% by weight, relative to the total weight of the composition.

Co-emulsifiers may be added to the composition according to the invention, if desired. When they are used, co-emulsifiers are added in a quantity ranging from 0.05% to 10% by weight, relative to the total weight of the composition. One co-emulsifier which may be mentioned is glyceryl stearate.

In dispersions of lipid vesicles, the emulsifier is constituted by ionic and/or nonionic lipid vesicles.

Oils which may be used in the invention include mineral oils (liquid petroleum), vegetable oils (Jojoba oil, apricot oil, sesame oil), synthetic oils (myristyl myristate, octyl palpitate, hydrogenated polyisobutene), silicone oils (cyclomethicone) and fluorinated oils (perfluoropolyethers). Fatty alcohols (cetyl alcohol) and fatty acids may be added to these oils.

Hydrophilic gelling agents which may be used include carboxyvinyl polymers, natural gums, and clays. Lipophilic gelling agents which may be used include modified clays such as bentones, metal salts of fatty acids, such as aluminum stearates, and hydrophobic silica.

Hydrophilic active agents which can be used include proteins or protein hydrolysates, amino acids, polyols, especially glycerol or sorbitol, urea, allantoin, sugars and sugar derivatives.

Lipophilic active agents which may be used include retinol (vitamin A) and derivatives thereof, tocopherol (vitamin E) and derivatives thereof, essential fatty acids, ceramides, essential oils, and salicylic acid and derivatives thereof.

Fillers which may be mentioned are microspheres such as the acrylic copolymers sold under the name Polytrap® by the company Dow Corning, polyamides such as Orgasol® sold by the company Atochem, and polyethylene powders. It is also possible to use natural fillers, such as talc, mica and hydroxyapatite.

If desired, UV filters with lipophilic or hydrophilic properties can be used in the present compositions, as well as the oxides of titanium and of zinc. It is also possible, optionally, to add hydroxy acids, in particular β-hydroxyacids, keto acids and α-hydroxy acids, and in particular those extracted from fruits, more especially when the composition is in the form of a W/O emulsion. In the latter case, since the aqueous phase is dispersed, the contact of the α-hydroxy acids with the skin is less extensive than when they are used in other conventional forms of compositions. It follows that the disadvantages associated with α-hydroxy acids indicated above are then lessened.

A trial on a panel of 10 people using the present composition has shown that, after one week of application to the inside of the elbow joint, a 2.5% solution of vinegar had no undesirable effect, and, in 9 cases out of 10, a 5% solution of vinegar or a 10% solution of vinegar had no undesirable effect. By way of comparison, a 2.5% solution of lactic acid was judged to be 100% undesirable because of the irritation which it caused.

Having generally described this invention, a further understanding can be obtained by reference to certain specific examples which are provided herein for purposes of illustration only and are not intended to be limiting unless otherwise specified.

EXAMPLES

The quantities noted below are given in % by weight.

Example 1

Day cream (O/W emulsion)

| Phase A: | |
|---|---|
| Sorbitan tristearate (emulsifier) | 0.9 |
| PEG-40 stearate (emulsifier) | 2.0 |
| Cetyl alcohol | 4.0 |
| Glyceryl stearate (co-emulsifier) | 3.0 |
| Myristyl myristate | 2.0 |
| Octyl palmitate | 2.0 |
| Hydrogenated polyisobutene | 8.3 |
| Phase B: | |
| Cyclomethicone | 10.0 |
| Phase C: | |
| Acrylic copolymer (Polytrap) | 0.2 |
| Phase D: | |
| Fragrance | 1.0 |
| Phase E: | |
| Wine vinegar (containing 6% acetic acid) | 5.0 |
| Preservative | 0.7 |
| Water | qs 100% |

Procedure:

The constituents of phase A were melted at a temperature of from 75° to 80° C. Subsequently, after having cooled the mixture to about 50° C., phase B and then phase C were added thereto with stirring. The mixture was stirred using a turbine stirrer, and phase E was introduced into the mixture at a temperature of 70° to 75° C. The resulting emulsion was then cooled, and phase D was introduced therein with stirring.

A beauty cream was obtained which acted against ageing. It was pleasant to use, spread well and left the skin soft and non-shiny.

Example 2

Night cream (W/O emulsion)

| Phase A: | |
|---|---|
| 4-Polyglycerol isostearate/cetyl dimethicone copolyol/hexyl laurate (Abil WE 09) | 4.0 |
| Apricot oil | 3.0 |
| Cyclomethicone | 10.0 |
| Phase B: | |
| Lactic acid | 0.5 |
| Wine vinegar (containing 6% acetic acid) | 4.0 |
| Phase C: | |
| Fragrance | 1.0 |
| Phase D: | |
| Preservative | 0.5 |
| Water | qs 100% |

Procedure:

The constituents of phase A were mixed with slow stirring at a temperature of from 40° to 50° C. Then phase B and subsequently phase D were added thereto with stirring. The mixture was stirred using a turbine stirrer for 15 minutes. The mixture was then cooled to 25° C. and phase C was added thereto.

A night cream was obtained which spread well, was nutritive and left a protective film on the skin.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the cosmetic treatment of the effects of ageing, comprising applying, to the skin of a subject in need thereof, an effective anti-ageing amount of a cosmetically acceptable composition comprising vinegar as the active anti-ageing agent in a cosmetically acceptable carrier, wherein said effective anti-ageing amount is an amount effective to treat wrinkles, lines, linear dull complexion, blemishes or a combination thereof.

2. The method of claim 1, wherein the vinegar is a member selected from the group consisting of wine vinegar, cider vinegar, lemon vinegar, blackberry vinegar and raspberry vinegar.

3. The method of claim 2, wherein the vinegar is wine vinegar.

4. The method of claim 1, wherein said effective amount of vinegar is from 1 to 50% by weight relative to the total weight of the composition.

5. The method of claim 4, wherein said effective amount of vinegar is from 3 to 10% by weight relative to the total weight of the composition.

6. The method of claim 1, wherein the composition is in a form selected from the group consisting of aqueous gels, oil-in-water (O/W) emulsions, water-in-oil (W/O) emulsions, lotions, ointments, solutions, and dispersions of spherules.

7. The method of claim 6, wherein the composition is present in the form of an oil-in-water (O/W) emulsion or a water-in-oil (W/O) emulsion.

8. The method of claim 1, further comprising one or more members selected from the group consisting of cosmetically acceptable pigments and dyes, emulsifiers, oils and adjuvants.

9. The method of claim 8, wherein said one or more cosmetically acceptable adjuvants are one or more members selected from the group consisting of hydrophilic gelling agents, lipophilic gelling agents, hydrophilic active agents, lipophilic active agents, preservatives, antioxidants, fragrances, fillers, screening agents and colorants.

10. The method of claim 8, wherein said cosmetically acceptable oils are one or more members selected from the group consisting of mineral oils, vegetable oils, synthetic oils, silicone oils and fluorinated oils.

11. A method for the treatment of blemishes which are morbid in origin, comprising applying, to a subject in need thereof, an effective amount of a dermatological composition comprising vinegar as effective agent for the treatment of blemishes which are morbid in origin, in a dermatologically acceptable carrier.

* * * * *

UNITED STATES PATENT AND TRADEMARK OFFICE
CERTIFICATE OF CORRECTION

PATENT NO.    :    5,560,916
DATED:        :    OCTOBER 1, 1996
INVENTOR(S)   :    CONSTANTIN KOULBANIS, et al

It is certified that error appears in the above-identified patent and that said Letters patent is hereby corrected as shown below:

Column 1, line 37, "(cf. "Les vinaigres"0 [Vinegars]" should read
--(cf. "Les vinaigres" [Vinegars]--.

Column 2, line 39, "10 inorganic salts", should read --inorganic salts"--.

Signed and Sealed this

Twenty-first Day of April, 1998

Attest:

BRUCE LEHMAN

*Attesting Officer*              *Commissioner of Patents and Trademarks*